(12) United States Patent
Fischer (10) Patent No.: US 10,716,602 B2
(45) Date of Patent: Jul. 21, 2020

(54) INSTRUMENT FOR GUIDING A ROD INTO AN IMPLANT RECEIVING AREA

(71) Applicant: Aesculap AG, Tuttlingen (DE)

(72) Inventor: Kay Fischer, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 16/092,657

(22) PCT Filed: Apr. 4, 2017

(86) PCT No.: PCT/EP2017/057965
§ 371 (c)(1),
(2) Date: Oct. 10, 2018

(87) PCT Pub. No.: WO2017/178283
PCT Pub. Date: Oct. 19, 2017

(65) Prior Publication Data
US 2019/0125417 A1    May 2, 2019

(30) Foreign Application Priority Data

Apr. 11, 2016  (DE) ........................ 10 2016 106 608

(51) Int. Cl.
*A61B 17/70*    (2006.01)
*A61B 17/00*    (2006.01)

(52) U.S. Cl.
CPC ..................... *A61B 17/7086* (2013.01); *A61B 2017/00477* (2013.01)

(58) Field of Classification Search
CPC .................. A61B 17/7076–7092; A61B 17/70
See application file for complete search history.

(56) References Cited

U.S. PATENT DOCUMENTS

| 5,720,751 A | 2/1998 | Jackson |
| 5,910,141 A | 6/1999 | Morrison et al. |

(Continued)

FOREIGN PATENT DOCUMENTS

| EP | 2878276 A2 | 6/2015 |
| WO | 2013009493 A2 | 1/2013 |

OTHER PUBLICATIONS

German Search Report for German Application No. 10 2016 106 608.7, with English Translation, dated Nov. 9, 2016, 14 pages.

(Continued)

*Primary Examiner* — Jacqueline T Johanas
*Assistant Examiner* — Michelle C Eckman (57) ABSTRACT

An instrument for guiding a rod into a receiving area of an implant includes a coupling unit for coupling the instrument to the implant, a rod provided with an outer thread that can be positioned axially relative to the coupling unit, and at least one inner threaded segment arranged in an axially fixed manner relative to the coupling unit that can be brought into engagement or out of engagement with the outer thread of the threaded rod. The threaded rod has a stop, and the instrument has a locking element which is arranged in an axially fixed manner relative to the coupling unit for interacting with the stop. The locking element can be positioned in a radial direction relative to the threaded rod and is pretensioned in the direction of the threaded rod to engage with the stop by a pretensioning element which applies a radial force.

20 Claims, 9 Drawing Sheets

(56) References Cited

U.S. PATENT DOCUMENTS

| | | | |
|---|---|---|---|
| 6,183,472 B1* | 2/2001 | Lutz | A61B 17/7032 606/104 |
| 6,648,888 B1* | 11/2003 | Shluzas | A61B 17/7086 606/86 A |
| 7,470,279 B2 | 12/2008 | Jackson | |
| 8,439,922 B1* | 5/2013 | Arnold | A61B 17/7082 606/86 A |
| 8,540,718 B2 | 9/2013 | Dauster et al. | |
| 8,591,515 B2 | 11/2013 | Jackson | |
| 8,845,649 B2 | 9/2014 | Jackson | |
| 8,894,662 B2 | 11/2014 | Varieur et al. | |
| 9,050,143 B2 | 6/2015 | May et al. | |
| 9,101,416 B2 | 8/2015 | Dunbar et al. | |
| 9,149,307 B2 | 10/2015 | Sandstrom et al. | |
| 9,198,692 B1* | 12/2015 | Doose | A61B 17/7032 |
| 9,198,698 B1* | 12/2015 | Doose | A61B 17/708 |
| 9,265,533 B2 | 2/2016 | Nelson et al. | |
| 9,486,256 B1* | 11/2016 | Lish | A61B 17/7086 |
| 9,532,815 B2 | 1/2017 | Jackson | |
| 9,629,661 B2 | 4/2017 | Kraus | |
| 9,636,151 B2 | 5/2017 | Jackson | |
| 9,636,152 B2 | 5/2017 | Daubs et al. | |
| 9,655,664 B2 | 5/2017 | Barrus et al. | |
| 9,901,378 B2 | 2/2018 | Dauster et al. | |
| 10,136,927 B1* | 11/2018 | Lish | A61B 17/7086 |
| 2007/0270867 A1* | 11/2007 | Miller | A61B 17/7088 606/86 R |
| 2008/0015601 A1* | 1/2008 | Castro | A61B 17/7086 606/86 R |
| 2008/0221626 A1* | 9/2008 | Butters | A61B 17/7086 606/86 A |
| 2008/0243190 A1* | 10/2008 | Dziedzic | A61B 17/7091 606/278 |
| 2008/0319477 A1* | 12/2008 | Justis | A61B 17/7089 606/232 |
| 2009/0018593 A1* | 1/2009 | Barrus | A61B 17/7086 606/86 A |
| 2009/0157125 A1* | 6/2009 | Hoffman | A61B 17/7086 606/86 A |
| 2011/0202096 A1* | 8/2011 | White | A61B 17/7032 606/86 R |
| 2011/0257692 A1* | 10/2011 | Sandstrom | A61B 17/7085 606/86 A |
| 2011/0313460 A1* | 12/2011 | McLean | A61B 17/7032 606/264 |
| 2012/0191144 A1* | 7/2012 | Peultier | A61B 17/7086 606/86 A |
| 2012/0271365 A1* | 10/2012 | Daubs | A61B 17/7085 606/86 A |
| 2012/0283786 A1* | 11/2012 | Rezach | A61B 17/7085 606/305 |
| 2013/0018419 A1* | 1/2013 | Rezach | A61B 17/7076 606/264 |
| 2013/0090697 A1* | 4/2013 | George | A61B 17/7091 606/305 |
| 2013/0245702 A1* | 9/2013 | McBride | A61B 17/7076 606/305 |
| 2014/0052187 A1* | 2/2014 | McBride | A61B 17/708 606/264 |
| 2014/0148865 A1* | 5/2014 | Hennard | A61B 17/7086 606/86 A |
| 2014/0163625 A1* | 6/2014 | Meyer | A61B 17/7086 606/86 A |
| 2014/0277137 A1* | 9/2014 | Stad | A61B 17/7076 606/246 |
| 2014/0364912 A1* | 12/2014 | May | A61B 17/7043 606/253 |
| 2015/0066042 A1* | 3/2015 | Cummins | A61B 17/7037 606/104 |
| 2015/0066089 A1* | 3/2015 | Nelson | A61B 17/7083 606/265 |
| 2015/0100097 A1* | 4/2015 | Barrus | A61B 17/7086 606/86 A |
| 2015/0100098 A1* | 4/2015 | Moore | A61B 17/7086 606/86 A |
| 2015/0112392 A1* | 4/2015 | Anand | A61B 17/7011 606/279 |
| 2015/0142067 A1 | 5/2015 | Bess et al. | |
| 2015/0173809 A1* | 6/2015 | Bechtel | A61B 17/7002 606/265 |
| 2016/0030093 A1 | 2/2016 | Walker | |
| 2016/0089188 A1* | 3/2016 | McBride, Jr. | A61B 17/7076 606/279 |
| 2016/0206354 A1* | 7/2016 | Mladenov | A61B 17/7002 |
| 2016/0228160 A1* | 8/2016 | Anand | A61B 17/7086 |
| 2016/0331420 A1 | 11/2016 | Dandanopoulos et al. | |
| 2016/0346011 A1* | 12/2016 | Angus | A61B 17/7032 |
| 2017/0027612 A1* | 2/2017 | Viart | A61B 17/708 |
| 2017/0252074 A1* | 9/2017 | Semingson | A61B 17/7085 |
| 2017/0319246 A1* | 11/2017 | Mladenov | A61B 17/7086 |
| 2017/0325855 A1* | 11/2017 | Roger | A61B 17/7086 |
| 2018/0153593 A1* | 6/2018 | Goel | A61B 17/7086 |
| 2018/0185072 A1* | 7/2018 | Rubin | A61B 17/708 |
| 2019/0069934 A1* | 3/2019 | Mickiewicz | A61B 17/708 |
| 2019/0125417 A1* | 5/2019 | Fischer | A61B 17/7086 |
| 2019/0247101 A1* | 8/2019 | Barrus | A61B 17/7086 |
| 2019/0274740 A1* | 9/2019 | Stoll | A61B 17/7086 |

OTHER PUBLICATIONS

International Search Report and Written Opinion for International Application No. PCT/EP2017/057965, dated Jul. 3, 2017, 16 pages.

\* cited by examiner

INSTRUMENT FOR GUIDING A ROD INTO AN IMPLANT RECEIVING AREA

RELATED APPLICATIONS

The present application is the United States national phase entry of International Application No. PCT/EP2017/057965, filed Apr. 4, 2017, which claims the benefit of priority of German Application No. 10 2016 106 608.7, filed Apr. 11, 2016. The contents of International Application No. PCT/EP2017/057965 and German Application No. 10 2016 106 608.7 are incorporated by reference herein in their entireties.

FIELD

The present invention relates to an instrument for guiding a rod into a receiving area of an implant, in particular a pedicle screw, comprising a coupling unit for coupling the instrument to the implant, in particular to a head of the pedicle screw, a rod pusher unit comprising a threaded rod which is provided with an outer thread and can be positioned in axial direction relative to the coupling unit, as well as a rod pusher which is coupled or connected to the threaded rod in a rotatable but axially fixed manner, and at least one inner threaded segment arranged in an axially fixed manner relative to the coupling unit, wherein the inner threaded segment can be brought into engagement or out of engagement with the outer thread of the threaded rod.

BACKGROUND

Such instruments are used, for example, in open spine operations to create a fixed or rigid connection between pedicle screws screwed into different vertebrae using a rod. The instrument is used to insert rods, by means of which adjacent pedicle screws are fixed relative to each other, into their respective tulip and to hold them in this position so that the rod can be secured there with a set screw. In cases where the rod is placed far above the tulip and spaced from it, e.g. due to slipped vertebrae (spondylolisthesis), large forces may be required to force the rod into the tulip or to pull a slipped vertebral body into the desired position. Instruments are known for this with which the rod is positioned toward a pedicle screw head exclusively by screw actuation of the instrument. One part of the instrument grips the head of a pedicle screw and another part of the instrument rests on a rod to be pressed into the head. The two parts are coupled to each other via a threaded mechanism and can be brought closer together by screwing action so that the rod is pressed into the tulip of the pedicle screw head or the screw is pulled towards the rod. The disadvantage of such instruments is that complex and laborious adjustment is necessary due to pure screw actuation over long feed distances. In particular, this means that the instrument is extremely difficult to disassemble for cleaning purposes, as its parts that are coupled to one another via the threaded mechanism must always be completely screwed or unscrewed.

A well-known instrument with pure screw actuation has an implant receiving area, a threaded sleeve and a front handle. Implant receiving area, threaded sleeve and handle are arranged or designed to be torque-proof and axially fixed relative to each other. The instrument also has a rod pusher and a threaded rod, which are also axially fixed but coupled so that they can rotate relative to each other. Both components are mounted in the instrument so that they can be displaced relative to the implant receiving area. The threaded rod is provided with a handle at its proximal end facing away from the rod pusher and is in engagement with the threaded sleeve. It can be screwed into and out of the threaded sleeve by turning the handle. A translation performed in this way is transferred to the rod pusher as a result of the above-described coupling to the rod pusher, while the rod pusher does not rotate. As a result, the implant receiving area and the rod pusher are axially positioned relative to each other by the threaded rod being screwed in and out of the threaded sleeve. Dismantling for cleaning purposes is time-consuming.

Since the distance over which a rod must be pressed into a pedicle screw tulip by means of the instrument is usually larger than 25 mm, e.g. 45 mm, instruments with quick adjustment have been developed. One instrument of this type is known from US 2015/0100097 A1 or US 2015/0100098 A1, for example, and comprises a latching mechanism. A threaded rod engages in a spring-loaded threaded shell or threaded section that can be positioned relatively in the radial direction. With axial pressure on the threaded rod, the threaded shell/the threaded section is shifted against the spring preload in the radial direction (is deflected), so that the threaded rod can be pushed forward in the axial direction without screw movement until a counterpressure exerted by the rod becomes too high. From this point on, a further axial positioning can be carried out by means of screwing, whereby high forces can be transmitted to the rod. As soon as the rod has reached the desired end position, a set screw is screwed into the tulip and the rod is fixed in this way. The threads are released from each other and brought out of engagement by pressing a release knob, which is operatively connected to the threaded shell or the threaded section. The threaded rod is thus released and can be withdrawn. The advantages of this mechanism are largely fatigue-free work and time savings, since the entire axial positioning does not have to be carried out by screwing. However, since these instruments are able to exert compressive forces of several 1000 N, decoupling the threaded rod from the threaded shell under pressure presents a disadvantageous risk of injuring surrounding structures or operating room staff. Although the instrument is quick to disassemble due to its latching mechanism, it has the disadvantage that unintentional complete disassembly of the instrument may occur during decoupling, which is undesirable in a surgery in which several bone screws have to be braced.

One problem that many well-known instruments have is their suitability for cleaning. As a rule, the instruments are designed as slim as possible to minimize skin incisions. Accordingly, the individual components of the instrument are placed closely together and are difficult to access, which makes them difficult to clean.

SUMMARY

Against this background, the present invention is based on the object of providing an instrument for the relative positioning, guiding and insertion of a rod into a receiving area of an implant, in particular a pedicle screw, with which high compressive forces can be transferred between rod and implant, and which is also suitable for large initial distances between rod and implant. The instrument should be easy to disassemble for cleaning purposes, but unintentional disassembly should always be reliably avoided. Danger and injury to structures adjacent to the instrument and to operating room staff should be excluded or at least minimized.

According to the present invention, this object is achieved by an instrument that is characterized in that the rod pusher unit has a stop and the instrument has a locking element arranged axially fixed relative to the coupling unit for interaction with the stop, which locking element can be positioned in the radial direction with respect to the threaded rod and is pretensioned toward the threaded rod into engagement with the stop by a first pretensioning element applying a radial force. In the following description, the pretensioning element that pretensions the locking element toward the threaded rod is referred to as "first pretensioning element" in order to be able to distinguish it from any other pretensioning elements of embodiments of the instrument. However, the term "first pretensioning element" does not mean that the instrument must have a second pretensioning element or further pretensioning elements.

The longitudinal axes of the threaded rod and the rod pusher coincide, in other words, they are arranged one behind the other in the axial direction. The stop, which according to the invention can be arranged either on or in the threaded rod and/or on or in the rod pusher, can project outwards, especially in the radial direction. It is realized according to one embodiment of the invention in the form of a radial offset, a shoulder or a step. It is advantageous if it is fully circumferential, as this prevents unintentional loosening of the threaded rod regardless of its rotational positioning. The stop is preferably formed on the distal side of the outer thread.

Directions used in the description of the invention, such as axial, radial and tangential, are related to the threaded rod and its orientation. The terms "distal" and "proximal" refer to the instrument from the surgeon's viewpoint. In this sense, "close to the surgeon" or "pointing to the surgeon" means proximally, while distal means "spaced from the surgeon" or "facing away from the surgeon". If the instrument is used as intended, its longitudinal axis, i.e. also the longitudinal axis of the threaded rod, is essentially aligned in the direction of the longitudinal axis of a pedicle screw. It can therefore be said that both the instrument and the threaded rod have a distal and a proximal end.

The advantage of the present invention is that, on the one hand, high contact forces can be exerted on a rod to be pressed into a tulip due to the thread engagement between the threaded rod and the inner threaded segment with fine adjustment and, if necessary, self-locking of the thread. On the other hand, the instrument has a kind of quick adjustment which is effected by decoupling the thread engagement between the threaded rod and the inner threaded segment. Thus, the instrument does not have to be adjusted in a cumbersome manner over the entire adjustment range by relative screwing, but can be advanced and opened quickly, easily and without any effort by decoupling. A particular advantage is that, unlike known instruments, complete loosening of these two components is prevented safely and easily by ensuring that the locking element engages or comes into engagement with the stop due to its radial preload, despite the quick adjustment by decoupling the threaded rod and inner threaded segment. In this way, a kind of safety lock is formed. Complete disassembly is nevertheless possible quickly and easily by loosening the locking element from the engagement with the stop on the part of the user. This ensures that complete disassembly is not accidental, but always intentional.

When using the instrument according to the invention, the threaded rod can be quickly positioned in the axial direction by decoupling it from the inner threaded segment. The threaded rod can thus be advanced in axial direction without screwing motion until a counterpressure exerted by the rod becomes too high. From this point on, further axial positioning can be achieved by means of screwing, while high forces can be transmitted to the rod. As soon as the rod has reached the desired end position, it can be secured to the implant with a set screw or similar. To remove the instrument, the threaded rod—by unscrewing it from the inner threaded segment—can first be released so far until it is relieved of pressure. By uncoupling the outer thread of the threaded rod from the inner thread of the inner threaded segment, the threaded rod can then be retracted by means of a pure axial positioning. According to the invention, however, this free axial positioning ability is limited by the stop of the threaded rod and the locking element engaged or coming into engagement with it. A particular advantage of the invention is that, in addition to largely fatigue-free work and time savings, since not the entire axial positioning has to be done by screwing, it is not possible to unintentionally completely loosen or remove the threaded rod from the instrument.

Advantageous embodiments of the invention will be explained in more detail below.

One embodiment of the invention is characterized in that the outer diameter (maximum diameter) of the stop is smaller than the root diameter of the outer thread. This ensures that the engagement between the inner threaded segment and the stop is not possible. In this way, damage to the inner thread can be safely avoided. Moreover, when the threaded rod is completely removed from the instrument, it can be avoided that the inner threaded segment comes into engagement with the stop, making disassembly difficult.

It is particularly advantageous if an axial unthreaded section is formed in the threaded rod with an outer diameter smaller than the root diameter of the outer thread. According to the one embodiment, the axial length of such a section can be larger than the axial length of the inner thread of the inner threaded segment. The unthreaded section creates a kind of idle range in which the threaded rod can be turned relative to the inner threaded segment without feed in the axial direction. In this way, the instrument can be easily attached to a pedicle screw and prepared for pressing in the rod. The unthreaded section can be designed in particular on the distal side of the outer thread. A further embodiment of the invention provides that an unthreaded section is formed both distally and proximally.

One embodiment of the invention is characterized in that the instrument has an unlocking element which interacts with the locking element. The locking element can be moved outwards in the radial direction, in particular by a user actuating the unlocking element, possibly against the preload applied by the first pretensioning element, and can thus be decoupled from the stop. The unlocking element can preferably be positioned in the radial direction relative to the threaded rod.

According to a further embodiment, the unlocking element may be accommodated in a housing. Therein, it can be pretensioned in particular by means of a spring as the first pretensioning element in the direction away from the threaded rod, i.e. radially outwards. In a special embodiment, this spring is arranged between the locking element and the unlocking element and braces these two elements against each other. A preload of the locking element toward the threaded rod can be effected by the unlocking element being able to interact with a stop formed in the housing and constituting a limitation for a movement of the unlocking element radially away from the threaded rod. In this way, the unlocking element forms a kind of floating bearing or receiving area for the locking element.

It is of particular advantage if the locking element has a contact surface for the threaded rod, with which it can slide in axial direction on the threaded rod while resting against the head diameter (outer diameter) of the outer thread without coming into engagement with the outer thread. In this way, a functional separation of the safety lock from the thread adjustment is achieved, which ensures particularly simple operation of the instrument. Furthermore, the locking element may have an inlet surface arranged in the manner of an inclined plane, i.e. oriented obliquely to the longitudinal axis of the threaded rod, for contact with the distal end of the threaded rod, which facilitates insertion of the threaded rod into the instrument.

A further embodiment of the invention is characterized in that the inner threaded segment can be positioned in the radial direction relative to the threaded rod and is pretensioned toward the threaded rod by a second pretensioning element applying a radial force, the inner threaded segment preferably being received in the housing and pretensioned toward the threaded rod preferably by means of a spring as second pretensioning element. The inner threaded segment can be brought into engagement or out of engagement with the outer thread of the threaded rod in particular by radial positioning. When the inner threaded segment is positioned in the radial direction to the threaded rod, hereinafter also referred to as the first position, the outer thread of the threaded rod and the inner thread of the inner threaded segment are in engagement with each other. When the inner threaded segment is positioned radially away from the threaded rod, hereinafter also referred to as the second position, they are disengaged. In the second position, the threaded rod can therefore be freely positioned in axial direction relative to the inner threaded segment, i.e. axially in both the distal and proximal direction, in particular by user action.

In particular, the inner threaded segment can take the form of a threaded shell with an inner thread or inner thread section facing the threaded rod. In the context of the invention, the instrument has at least one inner threaded segment. It is also within the scope if the instrument has two, three or four inner threaded segments circumferentially spaced apart to ensure uniform thread engagement.

The inner threaded segment can be accommodated in the housing in which the locking element is also accommodated and the unlocking element is mounted. In particular, it may be preloaded toward the threaded rod by means of a spring which is guided on or in the housing and supported radially outwards.

An embodiment of the invention is characterized in that thread flanks of the threaded rod and thread flanks of the inner threaded segment, which face each other, each are formed to have an undercut. An undercut of a thread flank in the sense of the invention is to be understood as the formation of a thread flank in which a thread flank has an outer region in the radial direction which projects in the axial direction in relation to a radially inner region of the same thread flank. This may be the case, for example, if a rear engagement or groove is provided in a thread flank, or the angle of inclination a of a flank is negative (with a conventional metric thread, the angle of inclination of each flank is positive).

As a result of the undercut, the outer thread of the threaded rod and the inner thread of the inner threaded segment are interlocked when engaged. If a pressure exerted on the threaded rod acts in axial direction such that the undercut thread flanks of the threaded rod and inner threaded segment are pressed against each other, displacement of the inner threaded segment in the radial direction is therefore not possible. The thread is virtually secured and inhibited.

The "normal" thread flanks of the threaded rod opposite the undercut thread flanks of the threaded rod and the "normal" thread flanks of the inner threaded segment opposite the undercut thread flanks of the inner threaded segment can act in the sense of the invention as an inclined plane or a reversing gear if a correspondingly high axial pressure is exerted on the threaded rod. If an axial pressure that acts in the axial direction in such a way that the thread flanks (without undercut) of the threaded rod and inner threaded segment are pressed against each other is sufficiently high, the inner threaded segment is displaced or positioned outwards in the radial direction due to the thread flanks oriented at an angle to the axial direction. The outer thread of the threaded rod and the inner thread of the inner threaded segment are thus disengaged and the threaded rod can slip through in the axial direction. In this way a quick positioning of the threaded rod in axial direction is possible. On the whole, an axial displacement in the one direction is possible with this embodiment, while it is inhibited in the other, opposite axial direction by the undercut and the threaded rod can be moved in this direction only by screwing.

In one embodiment, a thread flank formed with an undercut may have a negative flank angle α which is inclined relative to a normal to the respective thread axis and lies preferably in a range from approx. −10° to approx. −1°, preferably from approx. −8° to approx. −2°, more preferably from approx. −6° to approx. −3° and even more preferably from approx. −5° to approx. −4°. It is obvious that the flank angles of the threaded rod are matched to those of the inner threaded segment.

It is particularly advantageous if the undercut flank angles of the threaded rod are arranged on the proximal side and the undercut flank angles of the threaded sleeve are arranged on the distal side. In this case, it is not possible to position the threaded rod in the proximal axial direction when the threads of threaded rod and inner threaded segment are in engagement. Loosening of the thread engagement by shifting the inner threaded segment radially outwards is not possible when the threaded rod is under compression load, as the undercut blocks such a movement. The engaged threads are secured. However, if the threaded rod is relieved of pressure by partially loosening and unscrewing it, the thread engagement can be loosened despite the undercut system, resulting in a slight displacement of the threaded rod in the distal axial direction.

In a further development of this embodiment, the thread flanks opposite to an undercut flank are each formed so as to have a positive flank angle (3. In this way, positioning of the threaded rod in the distal axial direction is also possible when the threads are in engagement, namely by applying a sufficiently high axial pressure to the threaded rod, at which the inner threaded segment is forced outwards in the radial direction against the preload acting on it via the positive flank angle of the distal flanks of the threaded rod and the proximal flanks of the inner threaded segment, which act in the manner of an inclined plane.

According to one embodiment of the invention, the locking element and the inner threaded segment are arranged on diametrically opposite sides of the threaded rod. The unlocking element can be positioned in a first direction, especially in the radial direction toward the threaded rod, and in a second direction, especially in the radial direction away from the threaded rod, by user actuation. In this way, either the inner thread of the inner threaded segment can be unlocked from the outer thread of the threaded rod or the locking element can be unlocked from the stop with a single unlocking element as user-side actuation unit. This is particularly user-friendly. In particular, when positioned in the first direction, the unlocking element can move the inner threaded segment away from the threaded rod against the radial force of the pretensioning element and bring it out of engagement with its outer thread, and, when positioned in the second direction, can move the locking element away from the threaded rod against the radial force of the pretensioning element and bring it out of engagement with its stop.

The coupling unit is designed to couple the instrument to the implant. The implant is preferably a pedicle screw screwed into a vertebra of a spine. The coupling unit is preferably coupled to a pedicle screw head. To couple the instrument to the implant, the coupling unit may form or have an implant receiving area. Such an implant receiving area may include in particular two or three opposing coupling arms. These are provided with a coupling structure at their respective distal end. At least the distal ends of the coupling anus can be spaced apart or spread apart in the radial direction, can be arranged on an implant in the spaced state and coupled to it by closing the distal ends of the coupling arms and fixedly arranged thereon.

The threaded rod can be designed for direct or indirect contact with a rod to be pressed into an implant. In the latter case, it can be connected to a rod pusher unit or a rod pusher element and contact and position/shift the rod via the latter. Preferably, the threaded rod and the rod pusher are rotatably coupled to each other so that rotations of the threaded rod around its longitudinal axis are not transmitted to the rod during screwing.

In one embodiment, the rod pusher unit can interact with the coupling anus of the coupling unit, for example by passing the coupling arms through openings in the rod pusher unit so that the coupling arms are automatically closed when the rod pusher unit is positioned in the distal direction or are secured to the implant in the closed state.

It is advantageous during screwing a set screw into the implant or pedicle screw if the threaded rod is hollow with a passage channel continuously extending in the axial direction. The passage channel is dimensioned in such a way that the set screw and an instrument for screwing in the set screw fit through it.

It can also be said that the invention relates to an above-mentioned instrument comprising a latching mechanism in an improved four with further safety features. The invention offers the following advantages in particular: it enables space-saving push/pull knob operation for unlocking and dismantling, it can be dismantled for cleaning, it has few components and thus a reduced weight, and finally it is easy to operate.

BRIEF DESCRIPTION OF THE DRAWING FIGURES

Further features and advantages of the present invention will be apparent from the following exemplary and non-restrictive description of the invention on the basis of Figures. These are only schematic in nature and serve only to understand the invention. In the Figures.

DETAILED DESCRIPTION

Figure 1:
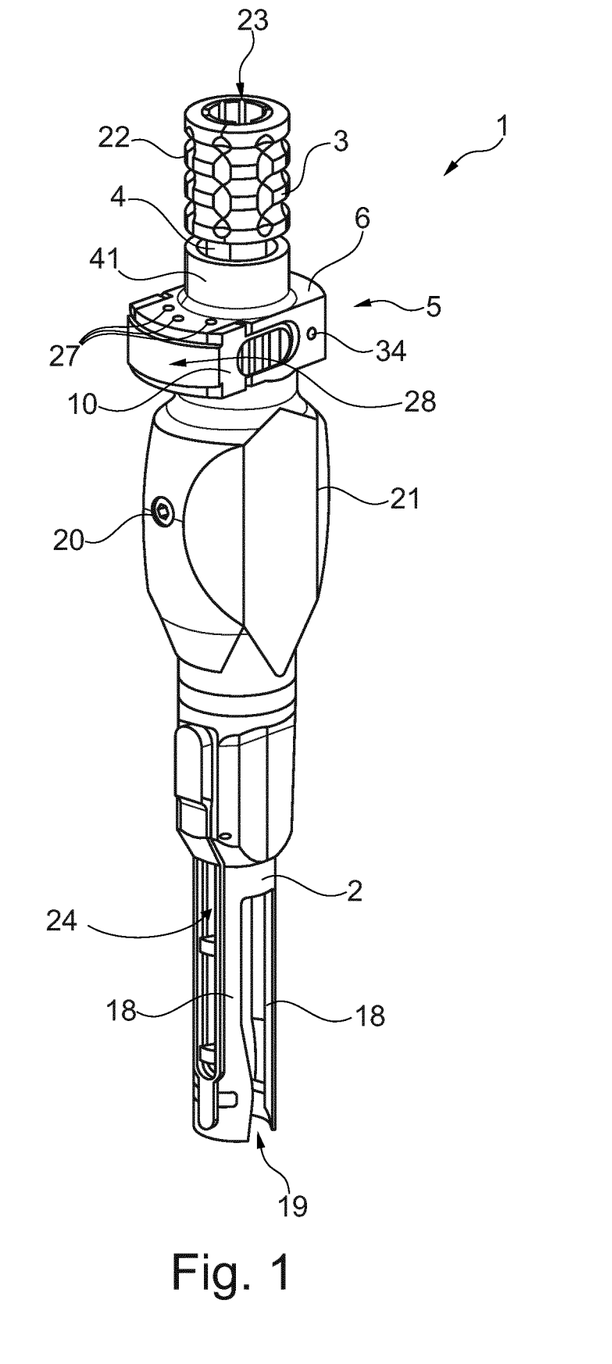
FIG. 1 shows an instrument according to the invention in a perspective view.

FIG. 1 shows an instrument 1 according to the invention for relative positioning and/or guiding and/or inserting a rod (not shown in the Figures) into a receiving area of an implant (likewise not shown), such as into a head of a pedicle screw, illustrated in a perspective view. The instrument 1 essentially comprises a coupling unit 2, a threaded rod 4 provided with an outer thread 3 and positionable in the axial direction relative to the coupling unit 2, and a latching mechanism 5 which is arranged to be axially fixed relative to the coupling unit 2.

Figure 2:
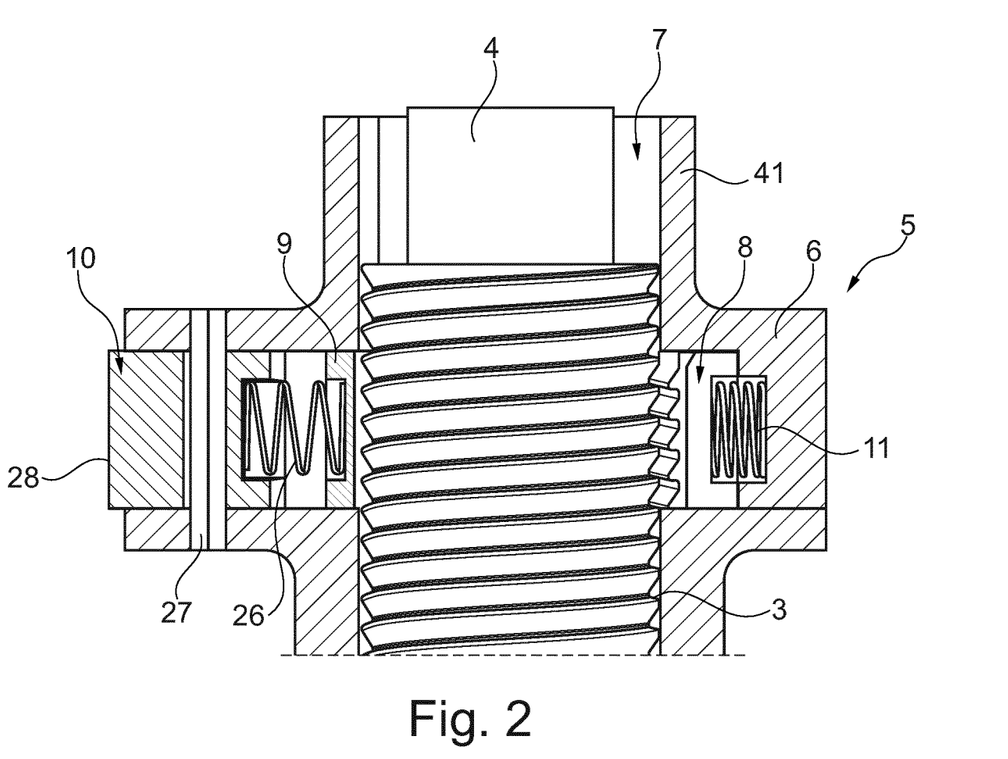
FIG. 2 is a sectional view of a latching mechanism of the instrument of FIG. 1 in the direction of the longitudinal axis of the instrument.

The latching mechanism 5 together with a section of the threaded rod 4 is shown on an enlarged scale in FIG. 2, among others. It essentially has a housing 6 with a through opening 7 extending in the axial direction, an inner threaded segment 8, a locking element 9 and an unlocking element 10. The housing 6 has a cylindrical guide 41 by means of which the threaded rod 4 is guided and positioned relative to the housing 6 and the units accommodated and supported therein.

The inner threaded segment 8 can be positioned in the radial direction relative to the threaded rod 4 and is pretensioned toward the threaded rod 4 by a pretensioning element 11 (second pretensioning element) in the form of a compression spring 11 which applies a radial force. Due to the radial positioning ability, the inner threaded segment 8 can be brought into engagement or out of engagement with the outer thread 3 of the threaded rod 4 by shifting or placing it in the radial direction.

Figure 16:
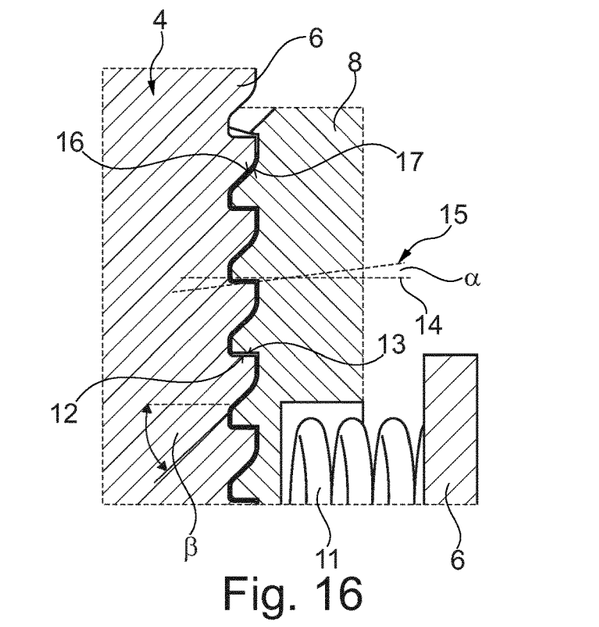
FIG. 16 shows a partial section through the inner and outer thread.

Thread flanks 12 of the threaded rod 4 and thread flanks 13 of the inner threaded segment 8, which face each other, are each formed so as to have an undercut. To illustrate the undercut, see FIG. 16 in particular, a normal 14 to the longitudinal axis of the threaded rod 4 is drawn. Also drawn is a line 15 which coincides with the thread flanks 12, 13. A negative flank angle α extends between the normal 14 and the line 15. Each thread flank 16 opposite an undercut thread flank 12 of the outer thread 3 of the threaded rod 4 is realized with a positive flank angle β. Likewise, each thread flank 17 opposite an undercut thread flank 13 of the inner threaded segment 8 is realized with a positive flank angle β

FIG. 1 shows that the coupling unit 2 has two opposing coupling arms 18, each of which is provided with a coupling structure 19 at its distal end, for an at least axially fixed coupling of the instrument 1 to the head of a pedicle screw. The coupling unit 2 is connected to a distal handle element 21 in a torque-proof and axially fixed manner by means of screws or rivets 20. The handle element 21, in turn, is connected to the housing 6 of the latching mechanism 5 in a torque-proof and axially fixed manner.

FIG. 2 shows that the threaded rod 4 is arranged in the through opening 7 of the housing 6. The threaded rod 4 is provided at its proximal end with a proximal handle element (not shown in the Figures), which is coupled to the threaded rod 4 in a torque-proof manner via a receiving area 22, and for its part is provided in the form of a substantially hollow cylinder with a passage channel 23 continuously extending in the axial direction. At its distal end, the threaded rod 4 is connected to a rod pusher 24 in an axially fixed manner. The threaded rod 4 and the rod pusher 24 can be rotated relative to each other about the longitudinal axis of the threaded rod 4.

On the whole, it can be said that the coupling unit 2, the distal handle element 21 and the housing 6 with the inner threaded segment 8 received therein, the locking element 9 which can also be referred to as a locking latch, and the unlocking element 10 form a first unit of the instrument 1. Similarly, the threaded rod 4, the rod pusher 24 and the proximal handle element form a second unit of the instrument 1. The first unit and the second unit of the instrument are coupled to each other by an engagement of the outer thread 3 of the threaded rod 4 in the inner thread 25 of the inner threaded segment 8.

Figure 3:
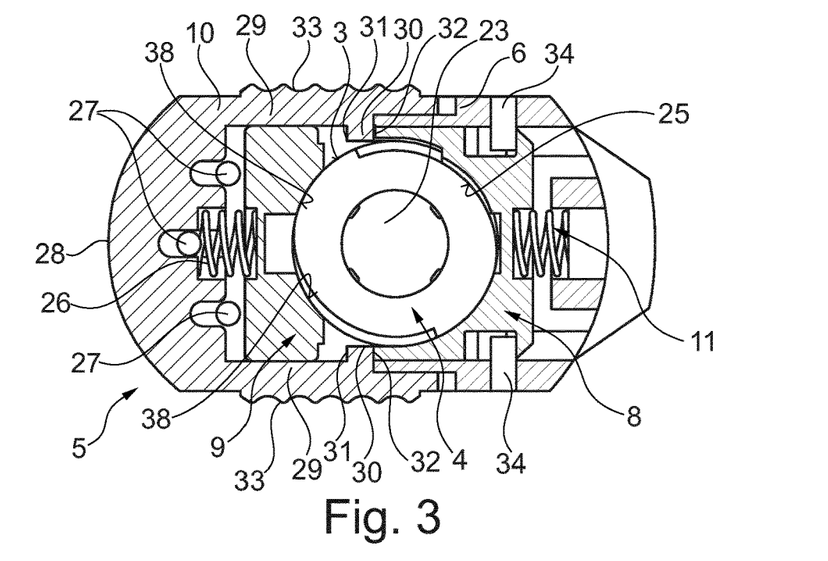
FIG. 3 is a sectional view of the latching mechanism of FIG. 2 transverse to the axial direction in a first functional position.
Figure 4:
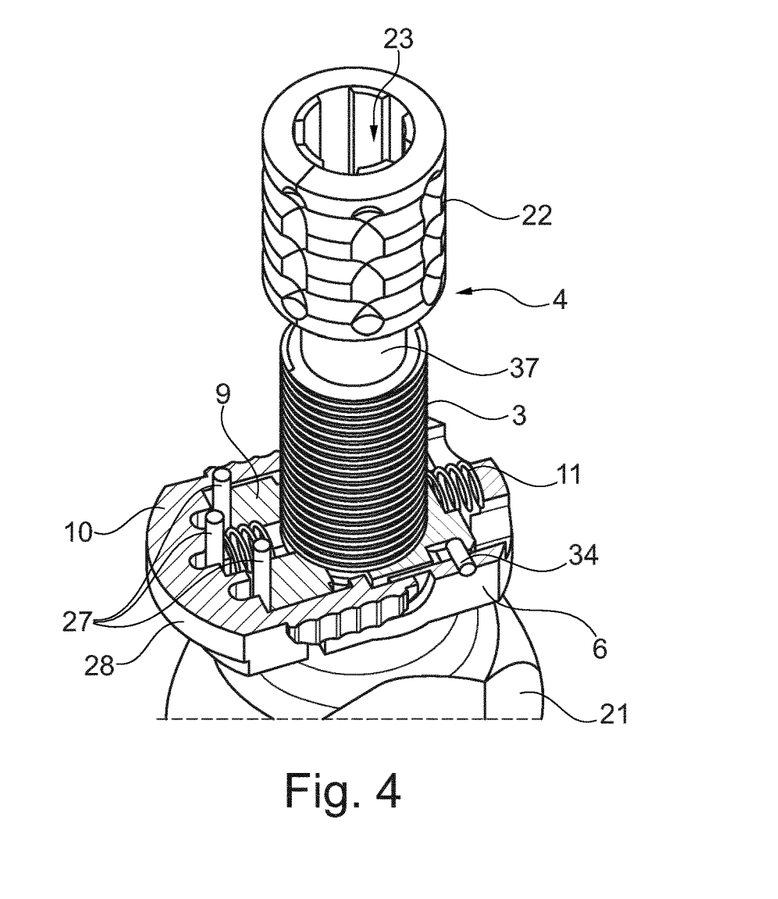
FIG. 4 is a perspective, partially cut open view of the latching mechanism of FIG. 2 in the first functional position.
Figure 13:
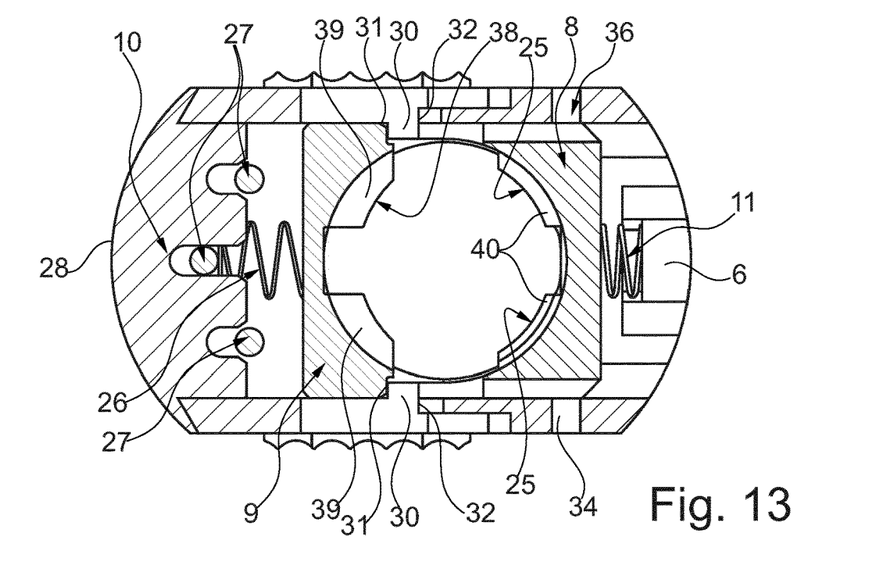
FIG. 13 is a top view of the mechanism of the instrument without threaded rod.
Figure 14:
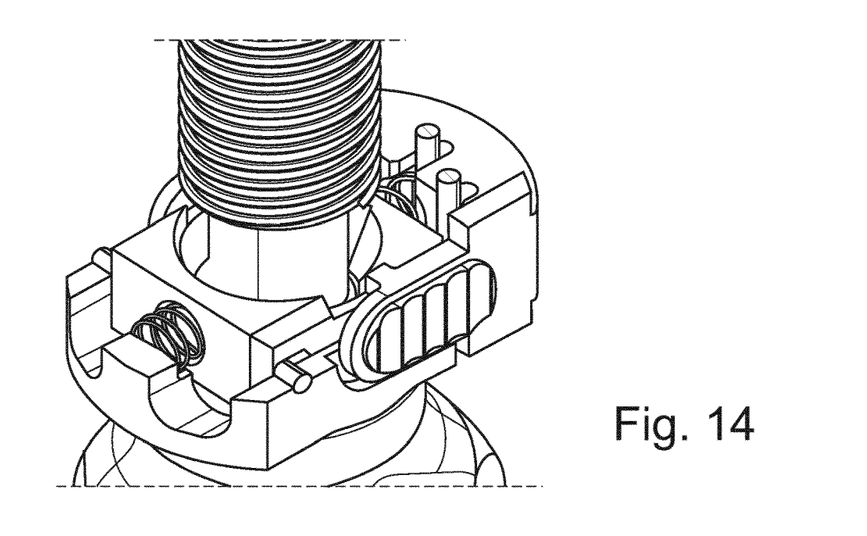
FIG. 14 is a perspective view of the mechanism without housing, FIG. 15 corresponds to the view of FIG. 14 with a partially cut housing.
Figure 15:
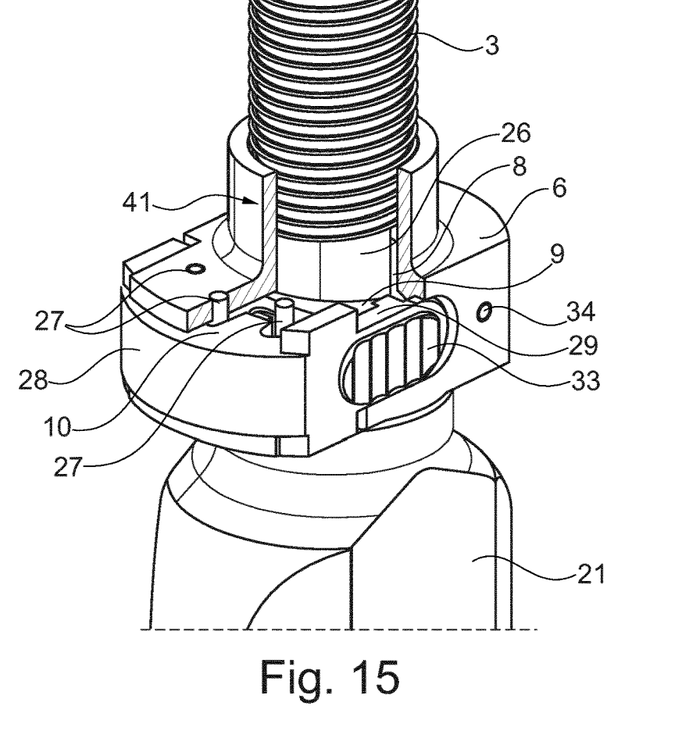

The inner threaded segment 8 is pretensioned inwards in the radial direction, i.e. toward the threaded rod 7, by means of the spring 11. This spring is supported radially outside on the housing 6. The locking element 8 is pretensioned against the threaded rod 4 in the radial direction by means of a compression spring 26 (first pretensioning element). In the state of rest, the compression spring 26 is supported radially outside on a central one of three guide pins 27. These support an unlocking element 10 so as to be able to be positioned in the radial direction in the housing 6, the radially outer end of which projects out of the housing 6 and is designed as an operating knob 28. In the above-mentioned state of rest, the unlocking element 10 is located radially spaced from the threaded rod 4 (FIG. 3). If the operating knob 28 is actuated, i.e. shifted radially toward the threaded rod 4, the compression spring 26 comes into contact with it and is supported by it. The unlocking element 10 has, see FIG. 13 in particular, two lateral arms 29 which extend tangentially to the threaded rod 4 on both sides of the knob 28. On each side facing the threaded rod 4, they have a stop pin 30 with a first stop face 31 and a second stop face 32. The first stop face 31 is designed to interact with the locking element 9 and the second stop face 32 to interact with the inner threaded segment 8. A handle structure 33 is formed on the outer sides of each arm 29 (see for example in FIG. 3). FIG. 13 shows that the inner threaded segment 8 is guided in the housing 6 by means of pins 34.

The radially inner end of the locking element 9 is provided with two contact surfaces 38 and sliding surfaces 39 arranged axially thereabove. The contact surfaces 38 are designed in such a way that the locking element 9 is able to rest on the outer shell surface (outer diameter) of the outer thread 3 of the threaded rod 4 and slide thereon in the axial direction without coming into engagement with the outer thread 3. The sliding surfaces 39 facilitate the axial insertion of the threaded rod 4.

Figure 12:
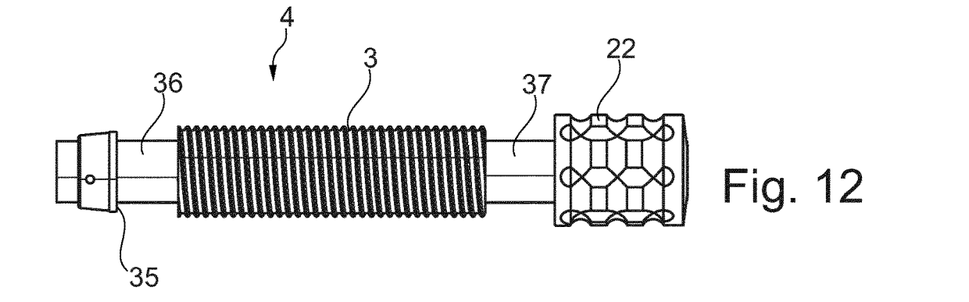
FIG. 12 is a side view of a section of the threaded rod.

Since the threaded rod 4 usually has to be retracted several times during a surgical operation, for example in order to press a rod into several pedicle screws, the invention provides that the instrument 1 will not unintentionally disassemble. For this purpose, the threaded rod 4 is designed with a stop 35 (see FIG. 12 in particular). At a point distally of the outer thread 3, an unthreaded section 36 is provided. Its diameter is smaller than the root diameter (inner diameter) of the outer thread 3. The stop 35 is located distal to the unthreaded section 36. A second unthreaded section 37, which is without function in the present example, is formed proximal to the outer thread 3.

The instrument 1 is used as follows:

First, the threaded rod 4 is inserted into the through opening 7 of the housing 6. In this process, its distal end comes into contact with the sliding surfaces 39 of the locking element 9, whereby the locking element 9 is pushed radially outwards against the tension of the spring 11. The same applies to the inner threaded segment 8, which has similar sliding surfaces 40. The threaded rod 4 is now inserted in the through opening 7 of the housing 6 and is in thread engagement with the inner threaded segment 8.

With the threaded rod 4 in the mounted state, the instrument 1 is coupled to the pedicle screw in an initial situation. At the beginning of a procedure for pressing a rod against a pedicle screw, the second unit consisting of the proximal handle element 22, the threaded rod 4 and the rod pusher 24 is pulled out in the proximal direction from the first unit already described. In this state, the instrument 1 is arranged with the coupling structure 19 at the head of the pedicle screw and coupled to it, whereby the rod to be pressed in is placed between the two coupling arms 18.

The threaded rod 4 is then inserted into the instrument 1 in the distal axial direction. Due to the positive flank angles β described above, the threaded rod 4 can be pushed by hand in the distal direction (downwards) by pure axial displacement. In this process, the inner threaded segment 8 is pressed radially outwards by the positive flank angles β through the outer thread 3 until the threaded rod 4 and the inner threaded segment 8 are out of engagement. The threaded rod can be axially displaced until it or the rod pusher 24 rests against the pedicle screw. The thread engagement is restored as a result of the radial preload by the spring 11. Further axial positioning is now achieved by turning the threaded rod 4 and unscrewing it from the inner threaded segment 8.

If the threads engage with each other again, they "get caught" as a result of the undercut. On the whole, the undercut of the thread has the effect that the threaded rod 4 can be pushed through the housing in one direction without any screwing movement, namely in the present exemplary embodiment in the distal direction (with displacement of the inner threaded segment 8 radially outwards), whereas a pure axial movement in the other direction (proximal) is prevented. This has the advantage that the threaded rod 4 connected to the rod pusher 24 can be inserted by hand in the distal direction so far until the counterforce exerted by the rod on the rod pusher 24 becomes too large. Subsequently, a further infeed in the distal direction occurs by screwing in the threaded rod 4. In the operations described above, the threaded rod 4 can be released in any position due to the undercut thread and the resulting self-locking effect and still retains the position.

Since the latching mechanism 2 has an undercut thread, any unintentional disconnection of the outer thread 3 from the inner thread of the inner threaded segment 8, for example by unintentional spring deflection against the spring preload, is impossible, because a higher axial counter force on the rod results in a stronger interlocking of the thread flanks. Furthermore, as a result of the undercut, the unlocking element 10 is blocked by a contact between stop pins 30 and stop faces 31, as it further interacts with the inner threaded segment 8, whose movement is not possible due to the blocked undercut thread under load. Accidental unlocking is therefore not possible.

Once the rod has reached its intended position in the head of the pedicle screw by screwing the threaded rod 4 with respect to the inner threaded segment 8, a set screw not shown in the Figures is screwed tight through the passage channel 23 of the threaded rod 4. It holds the rod in the screw or in the head, so that the instrument 1 can now be released and uncoupled. To do this, the threaded rod 4 has to be turned first by a few turns against the screw-in direction.

The threaded rod 4 is friction-inhibited in an axial movement in the distal direction by itself and/or the rod pusher 24 being in frictional contact with an axially fixed element of the instrument 1, for example with the distal handle element 21. The friction-based inhibition is dimensioned in such a way that an axial displacement of the threaded rod 4 is prevented when the threaded rod 4 is unscrewed from the inner threaded segment 8 without additional pressure load by the rod. As a result, the inner threaded segment 8 is displaced outwards in the radial direction against the preload of the spring 11. When the threaded rod 4 is sufficiently loosened and no more pressure is exerted on it by the rod (which is the case with the rod secured with the set-screw), the threads of the inner threaded segment 8 snap into the next thread of the outer thread 3 after approximately one revolution of the threaded rod 4, whereby an audibly perceptible click indicates to the user that the threaded rod 4 is relieved of pressure and he can safely unlock the threaded rod 4 by pressing the unlocking element 10, 28 and pull it back in the axial direction.

Figure 5:
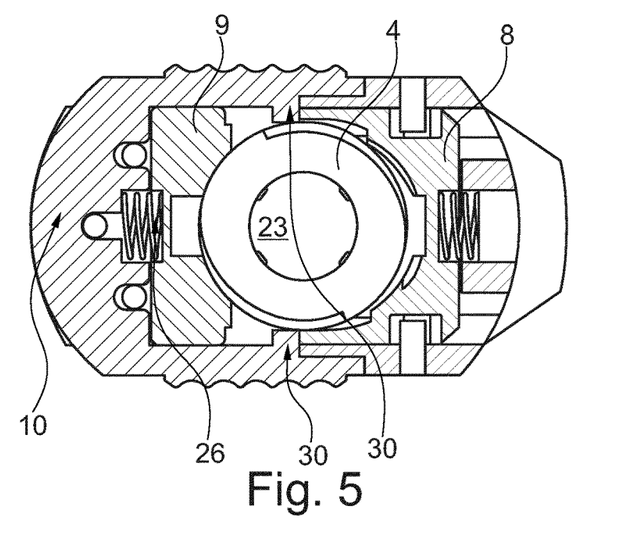
FIG. 5 is a sectional view of the latching mechanism of FIG. 2 transverse to the axial direction in a second functional position.
Figure 6:
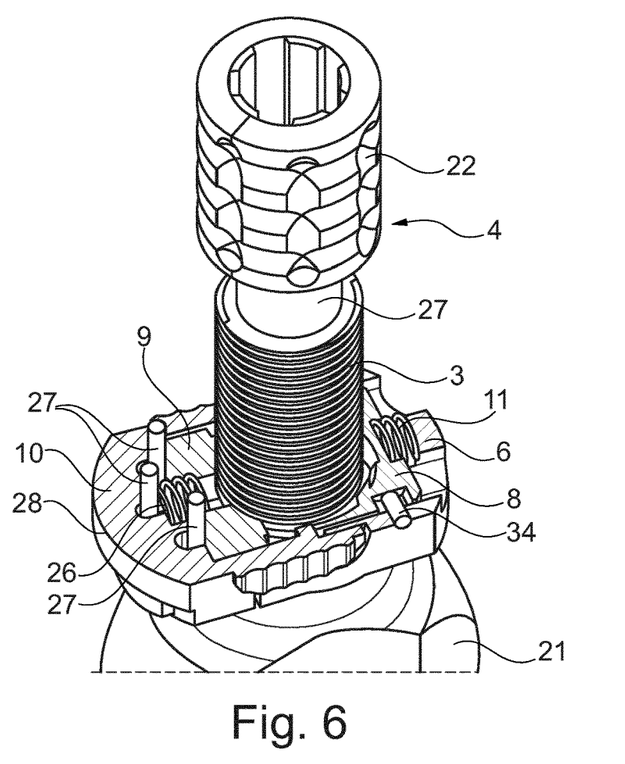
FIG. 6 is a perspective, partially cut open view of the latching mechanism of FIG. 2 in the second functional position.
Figure 7:
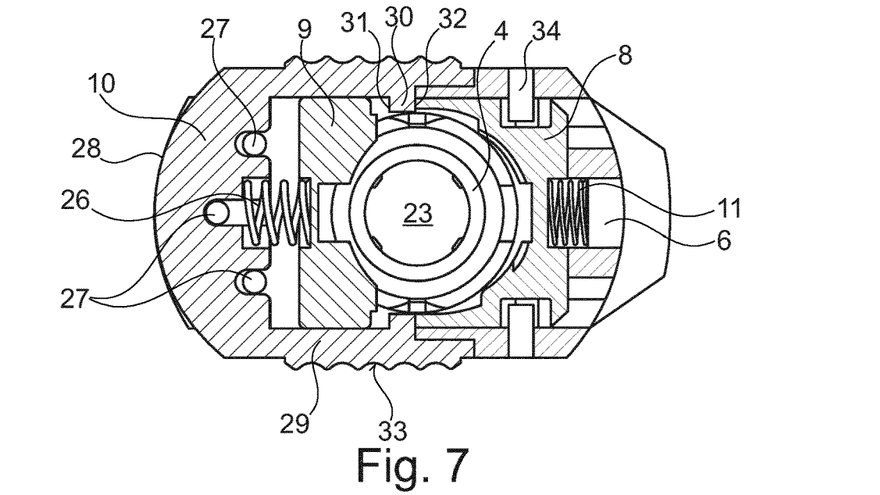
FIG. 7 is a sectional view of the latching mechanism of FIG. 2 transverse to the axial direction in a third functional position.
Figure 8:
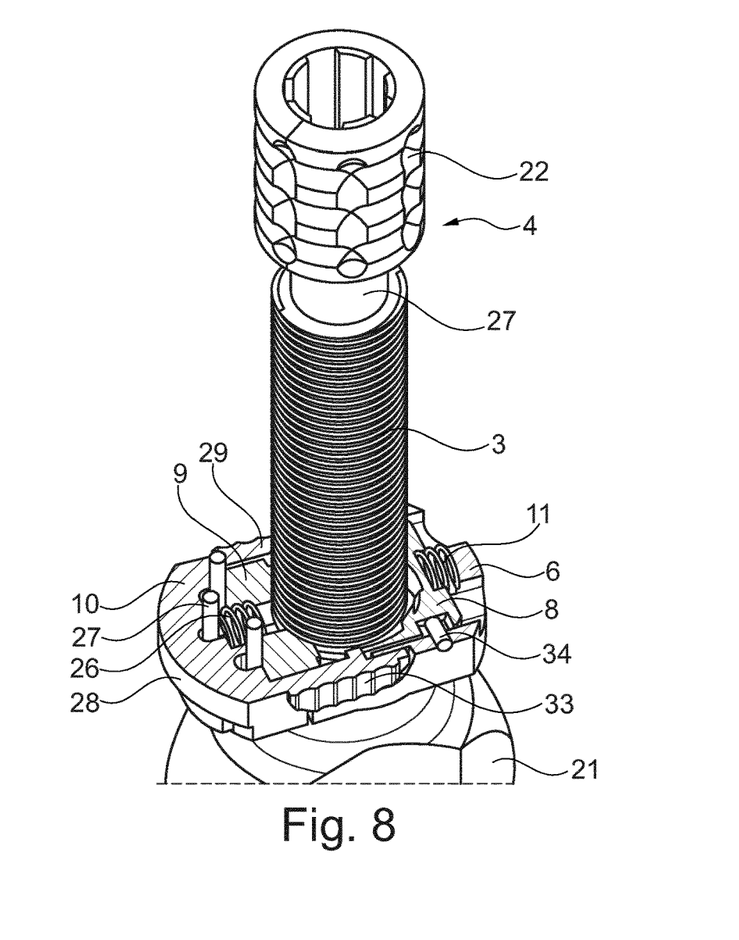
FIG. 8 is a perspective, partially cut open view of the latching mechanism of FIG. 2 in the third functional position.

For unlocking, the operator must press the knob 28 of the unlocking element 10 in the described exemplary embodiment in order to be able to retract the threaded rod 4 with a pure axial movement. The state when knob 28 is pressed to unlock the threads is shown in FIGS. 5 and 6. By pressing the knob 28, the actuating element 10 moves radially towards the threaded rod 4. Its stop pins 30 come into contact with the stop faces 32, so that the inner threaded segment 8 is pushed radially outwards away from the threaded rod 4 against the radial tension of the spring 11. In this way, the threads are disengaged. The threaded rod 4 can then be retracted into the initial position, i.e. in the proximal direction, by means of a purely axial movement.

Figure 9:
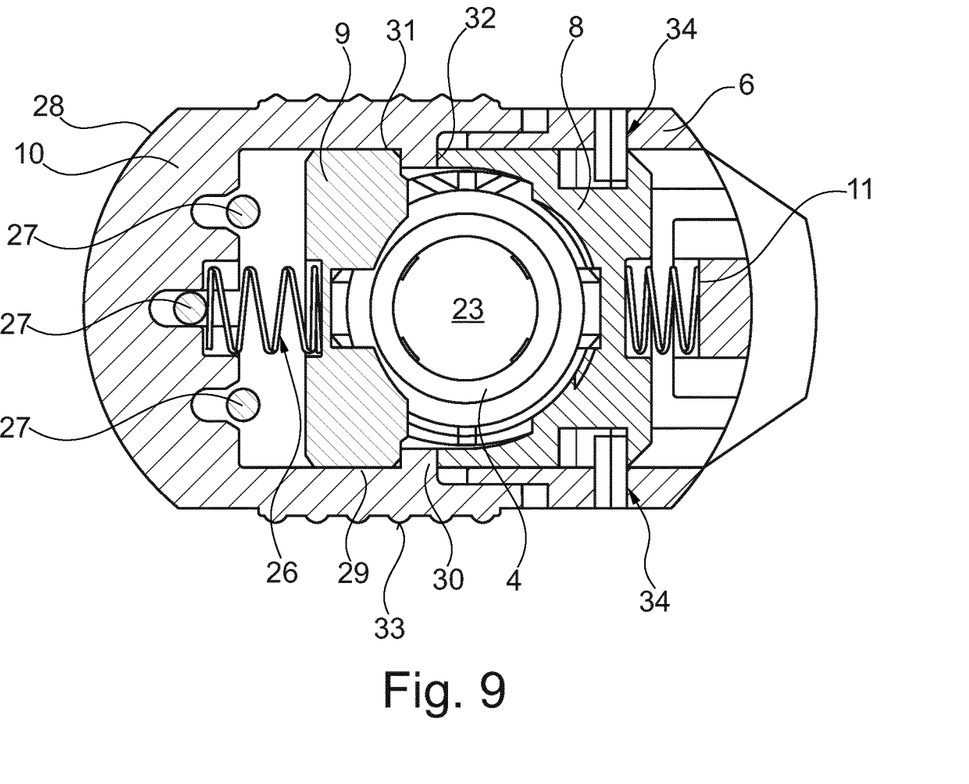
FIG. 9 is a sectional view of the latching mechanism of FIG. 2 transverse to the axial direction in a fourth functional position.
Figure 10:
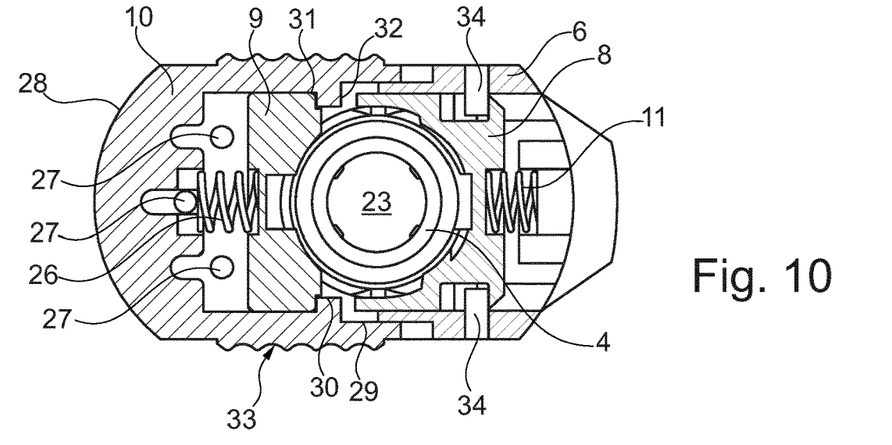
FIG. 10 is a sectional view of the latching mechanism of FIG. 2 transverse to the axial direction in a fifth functional position.
Figure 11:
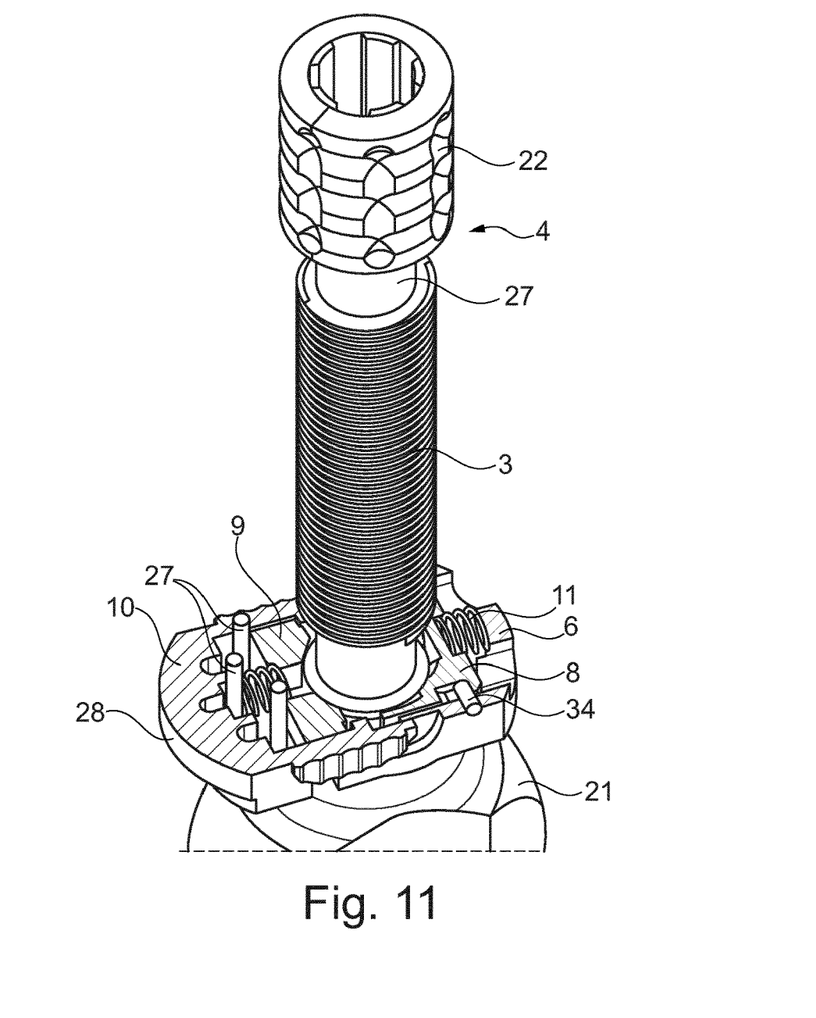
FIG. 11 is a perspective, partially cut open view of the latching mechanism of FIG. 2 in the fifth functional position.

However, due to the disassembly safety device according to the invention, the threaded rod 4 can only be retracted until the locking element 9 comes into contact with the stop 35 of the threaded rod 4. The radially inward pretensioning of the locking element 9 by means of the spring 26 supported on the actuating element continuously forces the locking element 9 toward the threaded rod 4. Its contact surfaces 38 slide off the outer diameter of the outer thread 3 until the threaded rod is relatively positioned in the axial direction such that the locking element 9 becomes overlapped with the unthreaded section 36. Due to its radial pretensioning, the locking element 9 snaps radially inwards (virtually into the unthreaded section) and comes into contact with the stop 35 during further axial movement of the threaded rod 4. Then, the threaded rod cannot be farther moved axially in the proximal direction, so that the instrument 1 is secured against unintentional complete disassembly of the threaded rod 4. The pretensioned spring 26 from the previous step favors safe snapping. Even if the knob 28 is now released (see FIG. 9), the mechanism is adjusted due to the continuous preload of the spring 26 such that the locking element 9 continues to engage in the unthreaded section 36, is in contact with the stop 35 of the threaded rod 4 and prevents unintentional disassembly. FIG. 9 also shows the purpose of the pins 34: To prevent the inner threaded segment 8 from engaging in the unthreaded section 36 when the knob 26 is released, it is held back radially outside by the pins 34.

After retracting the threaded rod 4, the instrument 1 can be placed on another pedicle screw and the application is repeated as described above until the rod has been pressed into all pedicle screws and fixed. The application cycles during a surgery are shown in FIGS. 3 to 9.

After the end of the surgery, the instrument 1 can be disassembled for cleaning despite the disassembly safety device. To this end, the actuating element 10 is pulled radially outwards, i.e. away from the threaded rod 4, by the ribbed handle structures 33 provided on the side for this purpose. This causes the stop pins 30 to come into contact with the stop faces 31 of the locking element 9 and, with continuous radial positioning, the locking element 9 is moved radially outwards until it is released from the stop 35 of the threaded rod 4. The threaded rod 4 is then fully released and can be completely removed from the housing 6 by pure axial movement.

Since the outer thread 3 has a larger diameter than the unthreaded section 36, the inner threaded segment 8 cannot snap into the undercut.

The invention claimed is:

1. An instrument for guiding a rod into a receiving area of an implant, the instrument comprising:
   a coupling unit for coupling the instrument to the implant,
   a rod pusher unit comprising a threaded rod which is provided with an outer thread and is configured to be positioned in an axial direction relative to the coupling unit, and a rod pusher which is coupled to the threaded rod in a rotatable but axially fixed manner; and
   at least one inner threaded segment arranged in an axially fixed manner relative to the coupling unit, wherein
   the at least one inner threaded segment is configured to be brought into engagement or out of engagement with the outer thread of the threaded rod,
   wherein
   the rod pusher unit has a stop that projects outwards in a radial direction; and
   the instrument has a locking element which is arranged in an axially fixed manner relative to the coupling unit for interacting with the stop, which locking element is configured to be positioned in a radial direction relative to the threaded rod and is pretensioned toward the threaded rod so as to engage with the stop by a pretensioning element which applies a radial force.

2. The instrument according to claim 1, wherein an outer diameter of the stop is smaller than a root diameter of the outer thread.

3. The instrument according to claim 2, wherein an axial unthreaded portion is formed in the threaded rod, an outer diameter of which is smaller than the root diameter of the outer thread and/or an axial length of which is larger than an axial length of an inner thread of the at least one inner thread segment.

4. The instrument according to claim 1, wherein an unthreaded portion is formed on a distal side of the outer thread.

5. The instrument according to claim 1, wherein the instrument has an unlocking element which interacts with the locking element in such a manner that the locking element, by actuation of the unlocking element, is moved outwards in the radial direction against a pretension applied by the pretensioning element and can thus be decoupled from the stop.

6. The instrument according to claim 5, wherein the unlocking element can be positioned in the radial direction relative to the threaded rod.

7. The instrument according to claim 6, wherein the unlocking element and the inner threaded segment are arranged on diametrically opposite sides of the threaded rod.

8. The instrument according to claim 6, wherein the unlocking element is configured to be positioned in a first direction by actuation and in a second direction.

9. The instrument according to claim 8, wherein, when positioned in the first direction, the unlocking element moves the at least one inner threaded segment away from the threaded rod against the radial force of a spring and brings it out of engagement with its outer thread, and, when positioned in the second direction, moves the locking element away from the threaded rod against the radial force of the pretensioning element and brings it out of engagement with the stop.

10. The instrument according to claim 5, wherein the unlocking element is received in a housing and is pretensioned by a spring so as to move away from the threaded rod.

11. The instrument according to claim 5, wherein the locking element has a contact surface for the threaded rod with which it can slide in the axial direction on the threaded rod while resting against a head diameter of the outer thread without coming into thread engagement with the outer thread.

12. The instrument according to claim 1, wherein thread flanks of the threaded rod and thread flanks of the at least one inner threaded segment, which face each other, are each formed so as to have an undercut.

13. The instrument according to claim 12, wherein flank angles of the threaded rod which are formed with an undercut are arranged on a proximal side and flank angles of the inner threaded segment which are formed with an undercut are arranged on a distal side.

14. The instrument according to claim 1, wherein the at least one inner threaded segment is configured to be positioned in the radial direction relative to the threaded rod and is pretensioned toward the threaded rod by a spring applying a radial force, the at least one inner threaded segment being received in the housing and pretensioned toward the threaded rod by the spring.

15. The instrument according to claim 1, wherein the threaded rod is hollow with a passage channel continuously extending in the axial direction.

16. An instrument for guiding a rod into a receiving area of an implant, the instrument comprising:
a coupling unit for coupling the instrument to the implant,
a rod pusher unit comprising a threaded rod which is provided with an outer thread and is configured to be positioned in an axial direction relative to the coupling unit, and a rod pusher which is coupled to the threaded rod in a rotatable but axially fixed manner; and
at least one inner threaded segment arranged in an axially fixed manner relative to the coupling unit, wherein
the at least one inner threaded segment is configured to be brought into engagement or out of engagement with the outer thread of the threaded rod,
wherein
the rod pusher unit has a stop; and
the instrument has a locking element which is arranged in an axially fixed manner relative to the coupling unit for interacting with the stop, which locking element is configured to be positioned in a radial direction relative to the threaded rod and is pretensioned toward the threaded rod so as to engage with the stop by a pretensioning element which applies a radial force,
wherein thread flanks of the threaded rod and thread flanks of the at least one inner threaded segment, which face each other, are each formed so as to have an undercut.

17. An instrument for guiding a rod into a receiving area of an implant, the instrument comprising:
a coupling unit for coupling the instrument to the implant,
a rod pusher unit comprising a threaded rod which is provided with an outer thread and is configured to be positioned in an axial direction relative to the coupling unit, and a rod pusher which is coupled to the threaded rod in a rotatable but axially fixed manner; and
at least one inner threaded segment arranged in an axially fixed manner relative to the coupling unit, wherein
the at least one inner threaded segment is configured to be brought into engagement or out of engagement with the outer thread of the threaded rod,
wherein
the rod pusher unit has a stop; and
the instrument has a locking element which is arranged in an axially fixed manner relative to the coupling unit for interacting with the stop, which locking element is configured to be positioned in a radial direction relative to the threaded rod and is pretensioned toward the threaded rod so as to engage with the stop by a pretensioning element which applies a radial force,
wherein an outer diameter of the stop is smaller than a root diameter of the outer thread, and
wherein an axial unthreaded portion is formed in the threaded rod, an outer diameter of which is smaller than the root diameter of the outer thread and/or an axial length of which is larger than an axial length of an inner thread of the at least one inner thread segment.

18. An instrument for guiding a rod into a receiving area of an implant, the instrument comprising:
a coupling unit for coupling the instrument to the implant,
a rod pusher unit comprising a threaded rod which is provided with an outer thread and is configured to be positioned in an axial direction relative to the coupling unit, and a rod pusher which is coupled to the threaded rod in a rotatable but axially fixed manner; and
at least one inner threaded segment arranged in an axially fixed manner relative to the coupling unit, wherein
the at least one inner threaded segment is configured to be brought into engagement or out of engagement with the outer thread of the threaded rod,
wherein
the rod pusher unit has a stop; and
the instrument has a locking element which is arranged in an axially fixed manner relative to the coupling unit for interacting with the stop, which locking element is configured to be positioned in a radial direction relative to the threaded rod and is pretensioned toward the threaded rod so as to engage with the stop by a pretensioning element which applies a radial force, wherein the instrument has an unlocking element which interacts with the locking element in such a manner that the locking element, by actuation of the unlocking element, is moved outwards in the radial direction against a pretension applied by the pretensioning element and can thus be decoupled from the stop, wherein the unlocking element can be positioned in the radial direction relative to the threaded rod, and wherein the unlocking element and the inner threaded segment are arranged on diametrically opposite sides of the threaded rod.

19. The instrument according to claim 18, wherein an outer diameter of the stop is smaller than a root diameter of the outer thread.

20. The instrument according to claim 19, wherein an axial unthreaded portion is formed in the threaded rod, an outer diameter of which is smaller than the root diameter of the outer thread and/or an axial length of which is larger than an axial length of an inner thread of the at least one inner thread segment.

* * * * *